US011065232B2

(12) United States Patent
Duffield et al.

(10) Patent No.: US 11,065,232 B2
(45) Date of Patent: Jul. 20, 2021

(54) DIHYDROTETRABENAZINE FOR THE TREATMENT OF ANXIETY AND PSYCHOSES

(71) Applicant: ADEPTIO PHARMACEUTICALS LIMITED, London (GB)

(72) Inventors: Andrew John Duffield, London (GB); Anant Pandya, London (GB)

(73) Assignee: ADEPTIO PHARMACEUTICALS LIMITED, London (GB)

( * ) Notice: Subject to any disclaimer, the term of this patent is extended or adjusted under 35 U.S.C. 154(b) by 0 days.

(21) Appl. No.: 16/498,697

(22) PCT Filed: Mar. 29, 2018

(86) PCT No.: PCT/EP2018/058126
§ 371 (c)(1),
(2) Date: Sep. 27, 2019

(87) PCT Pub. No.: WO2018/178262
PCT Pub. Date: Oct. 4, 2018

(65) Prior Publication Data
US 2020/0038384 A1 Feb. 6, 2020

(30) Foreign Application Priority Data

Apr. 1, 2017 (GB) .................................... 1705302

(51) Int. Cl.
*A61K 31/4375* (2006.01)
(52) U.S. Cl.
CPC ................ *A61K 31/4375* (2013.01)
(58) Field of Classification Search
CPC .................... A61K 31/4375; A61K 31/4745
See application file for complete search history.

(56) References Cited

U.S. PATENT DOCUMENTS

| 7,919,622 | B2 | 4/2011 | Amarasinghe et al. |
| 8,039,627 | B2 | 10/2011 | Gano |
| 2010/0087475 | A1 | 4/2010 | Duffield et al. |
| 2012/0003330 | A1 | 1/2012 | Gant et al. |
| 2018/0280359 | A1 | 10/2018 | Duffield et al. |
| 2018/0280360 | A1 | 10/2018 | Duffield et al. |
| 2018/0280361 | A1 | 10/2018 | Duffield et al. |
| 2018/0280374 | A1 | 10/2018 | Duffield et al. |
| 2018/0280375 | A1 | 10/2018 | Duffield et al. |
| 2019/0111035 | A1 | 4/2019 | Duffield et al. |

FOREIGN PATENT DOCUMENTS

| CN | 102285984 A | 12/2011 |
| GB | 800969 A | 9/1958 |
| WO | 2005077946 A1 | 8/2005 |
| WO | 2006053067 A2 | 5/2006 |
| WO | 2007007105 A1 | 1/2007 |
| WO | 2007017654 A1 | 2/2007 |
| WO | 2008058261 A1 | 5/2008 |
| WO | 2009073677 A1 | 6/2009 |
| WO | 2010018408 A2 | 2/2010 |
| WO | 2010026436 A2 | 3/2010 |
| WO | 2011153157 A2 | 12/2011 |
| WO | 2014047167 A1 | 3/2014 |
| WO | 2015120110 A2 | 8/2015 |
| WO | 2015171802 A1 | 11/2015 |
| WO | 2016127133 A1 | 8/2016 |
| WO | 2016210180 A2 | 12/2016 |
| WO | 2017112857 A1 | 6/2017 |
| WO | 2018140092 A1 | 8/2018 |
| WO | 2018140093 A1 | 8/2018 |
| WO | 2018140094 A1 | 8/2018 |
| WO | 2018140095 A2 | 8/2018 |
| WO | 2018140096 A1 | 8/2018 |

OTHER PUBLICATIONS

Yao, et al., "Preparation and Evaluation of Tetrabenazine Enantiomers and All Eight Stereoisomers of Dihydrotetrabenazine as VMAT2 Inhibitors", Eur. J. Med. Chem., 46, pp. 1841-1848, (2011).
Kilbourn, et al., "Binding of α-dihydrotetrabenazine to the Vesicular Monoamine Transporter is Stereospecific", Eur. J. Pharmacol., 278(3), pp. 249-252, (1995).
Bhatnagar, et al., "Pharmacokinetics of Dihydrotetrabenazine After Intravenous and Peroral Administration to Rats", Pharm Pharmacol Lett, 2(3), pp. 89-91, (1992).
Mehvar, et al., "Pharmacokinetics of Tetrabenazine and its Major Metabolite in Man and Rat", Drug Metab. Dispos., 15(2), pp. 250-255, (1987).
Roberts, et al., "The Pharmacokinetics of Tetrabenazine and its Hydroxy Metabolite in Patients Treated for Involuntary Movement Disorders", Eur. J. Clin. Pharmacol., 29, pp. 703-708., (1986).
Kilbourn, et al., "Absolute Configuration of (+)-α-Dihydrotetrabenazine, an Active Metabolite of Tetrabenazine", Chirality, 9, pp. 59-62, (1997).
Brossi, et al., "Syntheseversuche in der Emetin-Reihe, 3. Mitteilung", Helv. Chim Acta., vol. XLI, No. 193, pp. 1793-1806, (1958) (and English Translation).
Schwartz, et al, "Metabolic Studies of Tetrabenazine, a Psychotropic Drug in Animals and Man", Biochem. Pharmacol., 15, pp. 645-655, (1956).
Scherman, et al., "Hydrophobicity of the Tetrabenazine-Binding Site of the Chromaffin Granule Monoamine Transporter", Mol. Pharmacol., 33, pp. 72-77, (1987).
Mehvar, et al., "Concentration-Effect Relationships of Tetrabenazine and Dihydrotetrabenazine in the Rat", J. Pharm. Sci., 76(6), pp. 461-465, (1987).
Kilbourn, et al., "PET Radioligands for Vesicular Neurotransmitter Transporters", Med. Chem. Res., 5, pp. 113-126, (1994).
Kilbourn, "In Vivo Measures of Dopaminergic Radioligands in the Rat Brain: Equilibrium Infusion Studies", Synapse, 43, pp. 188-194, (2002).
Müller, "Valbenazine Granted Breakthrough Drug Status for Treating Tardive Dyskinesia", Expert Opin. Investig. Drugs, 24(6), pp. 737-742, (2015).

(Continued)

*Primary Examiner* — Deepak R Rao
(74) *Attorney, Agent, or Firm* — Heslin Rothenberg Farley & Mesiti P.C.

(57) ABSTRACT

This invention relates to pharmaceutical compositions containing (−)-β-dihydrotetrabenazine, processes for making them and their therapeutic uses.

10 Claims, No Drawings

(56) References Cited

OTHER PUBLICATIONS

Hauser, et al., "KINECT 3: A Randomised, Double-Blind Placebo-Controlled Phase 3 Trial of Valbenazine (NBI-98854) for Tardive Dyskinesia (PL02.003)", Neurology, (2016), 86(16 Supplement). Abstract.

Hauser, et al., "KINECT 3: A Phase 3 Randomised, Double-Blind, Placebo-Controlled Trial of Valbenazine for Tardive Dyskinesia", Am. J. Psychiatry, 174(5), pp. 476-484, (2017).

Ashcroft, et al., "A Comparison of Tetrabenazine and Chlorpromazine in Chronic Schizophrenia", Br. J. Psychiatry, 107(447), pp. 287-293, (1961).

Chen, et al., "Tetrabenazine for the Treatment of Hyperkinetic Movement Disorders: A Review of the Literature", Clin. Ther., 34(7), pp. 1487-1504, (2012).

Shen, et al., "Safety and Efficacy of Tetrabenazine and Use of Concomitant Medications During Long-Term, Open-Label Treatment of Chorea Associated with Huntington's and Other Diseases", Tremor Other Hyperkinet Mov, 3, pp. 1-13., (2013).

Skor, et al., "Differences in Dihydrotetrabenazine Isomer Concentrations Following Administration of Tetrabenazine and Valbenazine", Drugs R&D, 17(3), pp. 449-459, (2017).

"Archive History for NCT02844179 (+)-Alpha-Dihydrotetrabenazine Phase I" U.S. National Library of Medicine, https://clinicaltrials.gov/ct2/history/NCT02844179?V_1=View#StudyPageTop, (2016).

Kilbourn, "Rat pancreas uptake of [11C]dihydrotetrabenazine stereoisomers" Nucl. Med. Biol. (2010), 37(8), pp. 869-871.

Boldt et al., "Synthesis of (+)- and (−)Tetrabenazine from the Resolution of [alpha]-Dihydrotetrabenazine", Synth. Commun., (2009), 39(20), pp. 3574-3585.

Walkup, J.T., "A Guide to Tourette Syndrome Medications", https://depts.washington.edu/dbpeds/A%20Guide%20to%20TS%20Medications_M-313.pdf, pp. 1-14 (2008).

Great Britain Search Report for GB 1705302.6 dated Jan. 17, 2018.

DIHYDROTETRABENAZINE FOR THE TREATMENT OF ANXIETY AND PSYCHOSES

CROSS REFERENCE TO RELATED APPLICATIONS

This application is a national stage filing under section 371 of International Application No. PCT/EP2018/058126, filed on Mar. 29, 2018, and published on Oct. 4, 2018 as WO 2018/178262, which claims priority to Great Britain Application No. 1705302.6, filed on Apr. 1, 2017. The entire contents of WO 2018/178262 are hereby incorporated herein by reference.

This invention relates to pharmaceutical compositions containing (−)-β-dihydrotetrabenazine, processes for making them and their therapeutic uses.

BACKGROUND OF THE INVENTION

Psychosis is a generic psychiatric term for mental states in which the components of rational thought and perception are severely impaired. Persons experiencing a psychosis may experience hallucinations, hold paranoid or delusional beliefs, demonstrate personality changes and exhibit disorganized thinking. This is usually accompanied by a lack of insight into the unusual or bizarre nature of their behavior, difficulties with social interaction and impairments in carrying out the activities of daily living. Essentially, a psychotic episode involves loss of contact with reality.

Psychosis is often considered to be a symptom of severe mental illness. Although it is not exclusively linked to any particular psychological or physical state, it is particularly associated with schizophrenia, bipolar disorder (manic depression) and severe clinical depression. There are also several physical circumstances that can induce a psychotic state, including electrolyte disorder, urinary tract infections in the elderly, pain syndromes, drug toxicity, and drug withdrawal (especially alcohol, barbiturates, and sometimes benzodiazepines), as well as infections of or injuries to the brain (these psychoses are now more commonly referred to as organic mental disorders).

Psychosis may be caused by or follow brain injury and may occur after drug use, particularly after drug overdose, chronic use, and during drug withdrawal.

Chronic psychological stress is also known to cause psychotic states, although the exact mechanism by which this occurs is uncertain. Short-lived psychosis triggered by stress is known as brief reactive psychosis.

Psychotic episodes can be significantly coloured by mood. For example, people experiencing a psychotic episode in the context of depression may experience persecutory or self-blaming delusions or hallucinations, whilst people experiencing a psychotic episode in the context of mania may form grandiose delusions or have an experience of deep religious significance.

Hallucinations are defined as sensory perception in the absence of external stimuli. Psychotic hallucinations may occur in any of the five senses and take on almost any form, which may include simple sensations (such as lights, colours, tastes, smells) to more meaningful experiences such as seeing and interacting with fully formed animals and people, hearing voices and complex tactile sensations.

Auditory hallucinations, particularly the experience of hearing voices, are a common and often prominent feature of psychosis. Hallucinated voices may talk about, or to, the person, and may involve several speakers with distinct personas. Auditory hallucinations tend to be particularly distressing when they are derogatory, commanding or preoccupying.

Psychosis may involve delusional or paranoid beliefs. Psychotic delusions can be classified into primary and secondary types. Primary delusions are defined as arising out-of-the-blue and not being comprehensible in terms of normal mental processes, whereas secondary delusions may be understood as being influenced by the person's background or current situation.

Thought disorder describes an underlying disturbance to conscious thought and is classified largely by its effects on speech and writing. Affected persons may show pressure of speech (speaking incessantly and quickly), derailment or flight of ideas (switching topic mid-sentence or inappropriately), thought blocking, rhyming or punning.

One important and poorly understood feature of psychosis is usually an accompanying lack of insight into the unusual, strange or bizarre nature of the person's experience or behaviour. Even in the case of an acute psychosis, sufferers may seem completely unaware that their vivid hallucinations and impossible delusions are in any way unrealistic. However, insight can vary between individuals and throughout the duration of the psychotic episode. In some cases, particularly with auditory and visual hallucinations, the patient has good insight and this makes the psychotic experience even more terrifying in that the patient realizes that he or she should not be hearing voices, but does.

There are a number of possible causes for psychosis. Psychosis may be the result of an underlying mental illness such as Bipolar disorder (also known as manic depression), and schizophrenia. Psychosis may also be triggered or exacerbated by severe mental stress and high doses or chronic use of drugs such as amphetamines, LSD, PCP, cocaine or scopolamine. Sudden withdrawal from CNS depressant drugs, such as alcohol and benzodiazepines, may also trigger psychotic episodes. As can be seen from the wide variety of illnesses and conditions in which psychosis has been reported to arise (including for example, AIDS, leprosy, malaria and even mumps) there is no singular cause of a psychotic episode.

Schizophrenia is the name given to a group of psychotic disorders usually characterized by withdrawal from reality, illogical patterns of thinking, delusions, and hallucinations, and accompanied in varying degrees by other emotional, behavioral, or intellectual disturbances. Schizophrenia is associated with dopamine imbalances in the brain and defects of the frontal lobe and is caused by genetic and other biological factors and psychosocial factors.

The drugs traditionally used to treat psychoses such as those associated with schizophrenia (the so-called "typical" antipsychotics) effectively control the hallucinations, delusions, and confusion associated with these conditions. Such drugs, examples of which include haloperidol, chlorpromazine, and fluphenazine, have been available since the mid-1950s. These drugs act primarily by blocking dopamine receptors and are effective in treating the "positive" symptoms of psychosis.

Four major areas of the brain are involved as primary pathways for dopamine. They include the nigrostriatal, mesocortical, mesolimbic, and tuberoinfundibular systems. Decreased dopamine activity in the mesocortical tract (as seen in the schizophrenic patient) results in an inability for the prefrontal areas of the brain to activate. Positive symptoms, such as hallucinations and delusions, can occur when overactivity of dopamine in the mesolimbic tract occurs. There are five subcategories of dopamine receptors in the brain. Conventional antipsychotics have the greatest impact on the D2 receptor. The so-called "atypical" antipsychotic agents (see below) typically have a weaker effect on D2 receptors with more potent blockade on the D4 receptor which is mostly found in the frontal cortex and the hippocampus.

The atypical antipsychotics target the limbic area more specifically when blocking dopamine D2 receptors. Consequently, they have less impact on the nigrostriatal and mesocortical pathways, resulting in a reduced potential for adverse effects. As noted earlier, they also tend to have a greater affinity for dopamine D4 receptors.

The dopamine D4 receptor is a G protein-coupled receptor which is encoded by the DRD4 gene and is a synaptic neurotransmitter responsible for neuronal signalling in the mesolimbic system of the brain, an area of the brain that regulates emotion and complex behaviour (A. S. Woods, J. Signal Transduct. Res., 2010, 30(5), 331-336). D4 is a subtype of the D2 receptor and has structural, functional and pharmacological characteristics closely related to the D2 receptor.

The D4 receptor has been found to be highly expressed in limbic and cortical areas of the brain (Jardemark et al. Curr. Opin. Investig. Drugs, 2002, 3(1): 101-5). The atypical anti-psychotic drug clozapine has preferential affinity for the D4 receptors, suggesting the involvement of these receptors in schizophrenia. Consequently, there is considerable interest in dopamine D4 receptor antagonists as potential antipsychotics: see for example Faraci et al., Current Opinion in Chemical Biology, 1998, Vol. 2, Issue 4, 535-540, and Pugsley et al., Progress in Neuro-Psychopharmacology and Biological Psychiatry, 2002, Vol. 6, Issue 2, 219-226.

Anxiety is a physiological state characterized by a combination of cognitive, somatic, emotional, and behavioral components. Whereas it is a common emotion along with fear, anger, sadness, and happiness, and has a very important function in relation to survival, it can become pathological or maladaptive in some people.

Anxiety is often manifested as anger, fear, apprehension, or worry, and people suffering from anxiety may find that that they easily lose their patience, have difficulty concentrating, think constantly about the worst outcome in a given situation, have difficulty sleeping, become depressed and/or develop obsessive behaviour.

The mental symptoms of anxiety are frequently accompanied by physical symptoms such as heart palpitations, pale skin, sweating, nausea, chest pain, shortness of breath, stomach aches, headache, excessive thirst, flatulence, diarrhea, increased frequency of urination, sexual impotence, muscle pain, dizziness, pins and needles, tremors and painful or absent periods.

With the exception of panic attacks which are unpredictable and self limiting, anxiety can be generally classified according to cause or the circumstances in which the anxiety arises. One scheme that has been suggested classifies types of anxiety as follows:

1. Anxiety secondary to other psychiatric illness.
2. Primary anxiety neurosis which may have genetic influences.
3. Phobic anxiety which includes social phobias, general phobias and specific phobias.
4. Anxiety resulting from obsessional disorders. Excessive anxiety and anxiety disorders can be treated with anxiolytic drugs, examples of which are selective serotonin reuptake inhibitors (SSRIs), benzodiazepines and beta-receptor blockers such as propranolol and oxprenolol (which although not anxiolytics per se, can be used to combat the somatic symptoms of anxiety).

Examples of SSRIs include citalopram (Celexa, Cipramil, Emocal, Sepram, Seropram), escitalopram (Lexapro, Cipralex, Esertia), fluoxetine (Prozac, Fontex, Seromex, Seronil, Sarafem, Fluctin (EUR), Fluox (NZ)), fluvoxamine (Luvox, Faverin, Dumyrox), paroxetine (Paxil, Seroxat, Aropax, Deroxat, Rexetin, Xetanor, Paroxat), sertraline (Zoloft, Lustral, Serlain), and zimelidine (Zelmid, Normud), all of which are associated with any of a variety of adverse side effects.

Examples of benzodiazepines include lorazepam (Ativan), clonazepam (Klonopin), alprazolam (Xanax), and diazepam (Valium) and these are typically prescribed for short-term relief of severe and disabling anxiety. Benzodiazepines may also be administered to cover the latent periods associated with drugs prescribed to treat an underlying anxiety disorder. Benzodiazepines are also used as a longer term treatment for severe anxiety. However, there are problems associated with with the use of benzodiazepines, namely the risk of withdrawal symptoms and the risk of rebound syndrome after continuous usage of more than two weeks. In addition, there is the added potential problem of the accumulation of drug metabolites and adverse effects.

Buspirone (BuSpar) is a serotonin IA agonist which lacks the sedative side effects and the dependence associated with benzodiazepines and causes much less cognitive impairment. However, a disadvantage of buspirone is that 1 to 3 weeks can often elapse following administration before the anxiolytic effect of the drug becomes evident.

Other anxiolytics used in the past include barbiturates and meprobamate which exert an anxiolytic effect linked to the sedation they cause. However, the risk of abuse and addiction to these drugs is high and they are now largely obsolete as medications for treating anxiety. Thus, at the present time, there remains a need for alternative anxiolytic agents which lack all or some of the side effects associated with known anxiolytics.

Tetrabenazine (Chemical name: 1,3,4,6,7,11b-hexahydro-9,10-dimethoxy-3-(2-methylpropyl)-2H-benzo(a)quinolizin-2-one) has been in use as a pharmaceutical drug since the late 1950s. Initially used as an anti-psychotic, tetrabenazine is currently used for treating hyperkinetic movement disorders such as Huntington's disease, hemiballismus, senile chorea, tic, tardive dyskinesia and Tourette's syndrome, see for example Jankovic et al., Am. J. Psychiatry. (1999) August; 156(8):1279-81 and Jankovic et al., Neurology (1997) February; 48(2):358-62.

The primary pharmacological action of tetrabenazine is to reduce the supply of monoamines (e.g. dopamine, serotonin, and norepinephrine) in the central nervous system by inhibiting the human vesicular monoamine transporter isoform 2 (hVMAT2). The drug also blocks post-synaptic dopamine receptors.

The central effects of tetrabenazine closely resemble those of reserpine, but it differs from reserpine in that it lacks activity at the VMAT1 transporter. The lack of activity at the VMAT1 transporter means that tetrabenazine has less peripheral activity than reserpine and consequently does not produce VMAT1-related side effects such as hypotension.

Tetrabenazine is an effective and safe drug for the treatment of a variety of hyperkinetic movement disorders and, in contrast to typical neuroleptics, has not been demonstrated to cause tardive dyskinesia. Nevertheless, tetrabenazine does exhibit a number of dose-related side effects including causing depression, parkinsonism, drowsiness, nervousness or anxiety, insomnia and, in rare cases, neuroleptic malignant syndrome, see for example the introductory section of WO2016/127133 (Neurocrine Biosciences).

The chemical structure of tetrabenazine is as shown below.

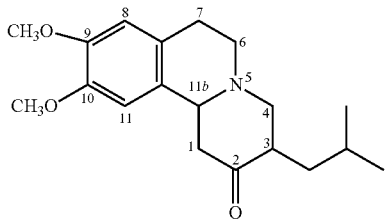

Structure of tetrabenazine

The compound has chiral centres at the 3 and 11b carbon atoms and hence can, theoretically, exist in a total of four isomeric forms, as shown below.

Possible tetrabenazine isomers

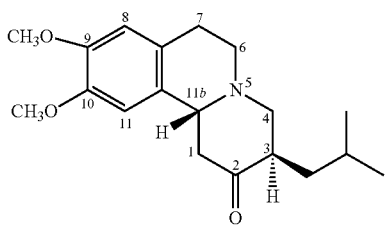

RR

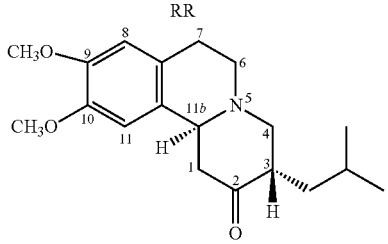

SS

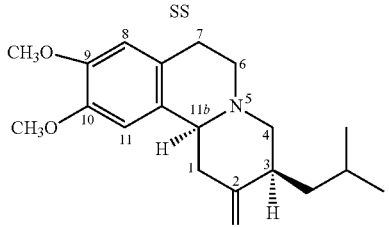

RS

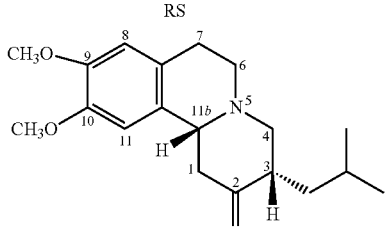

SR

The stereochemistry of each isomer is defined using the "R and S" nomenclature developed by Cahn, Ingold and Prelog, see *Advanced Organic Chemistry* by Jerry March, 4th Edition, John Wiley & Sons, New York, 1992, pages 109-114. In this patent application, the designations "R" or "S" are given in the order of the position numbers of the carbon atoms. Thus, for example, RS is a shorthand notation for 3R,11bS. Similarly, when three chiral centres are present, as in the dihydrotetrabenazines described below, the designations "R" or "S" are listed in the order of the carbon atoms 2, 3 and 11b. Thus, the 2R,3S,11bS isomer is referred to in short hand form as RSS and so on.

Commercially available tetrabenazine is a racemic mixture of the RR and SS isomers and it would appear that the RR and SS isomers are the most thermodynamically stable isomers.

Tetrabenazine has somewhat poor and variable bioavailability. It is extensively metabolised by first-pass metabolism, and little or no unchanged tetrabenazine is typically detected in the urine. It is known that at least some of the metabolites of tetrabenazine are dihydrotetrabenazines formed by reduction of the 2-keto group in tetrabenazine.

Dihydrotetrabenazine (Chemical name: 2-hydroxy-3-(2-methylpropyl)-1,3,4,6,7,11b-hexahydro-9,10-dimethoxy-benzo(a)quinolizine) has three chiral centres and can therefore exist in any of the following eight optical isomeric forms:

Dihydrotetrabenazine isomers

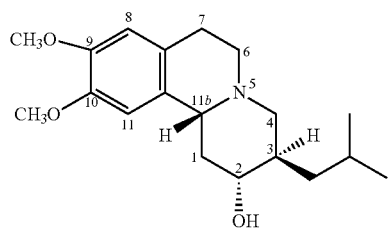

RRR

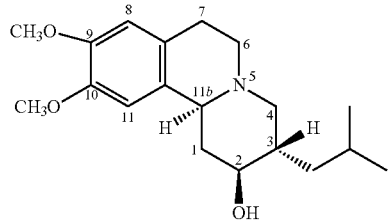

SSS

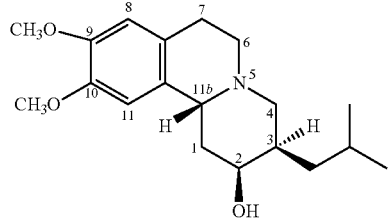

SRR

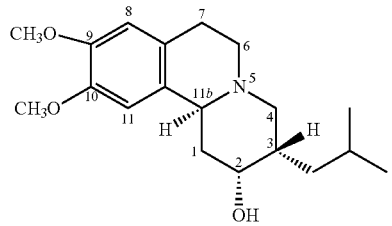

RSS

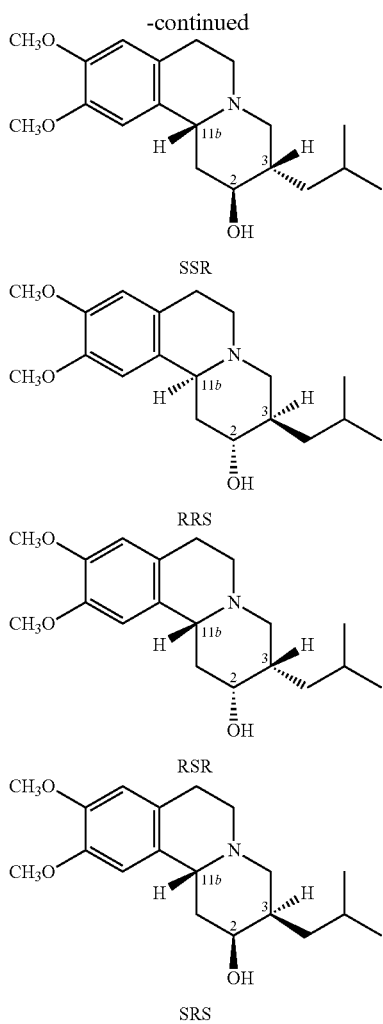

The synthesis and characterisation of all eight dihydrotetrabenazine isomers is described by Sun et al. (*Eur. J. Med. Chem.* (2011), 1841-1848).

Of the eight dihydrotetrabenazine isomers, four isomers are derived from the RR and SS isomers of the parent tetrabenazine, namely the RRR, SSS, SRR and RSS isomers.

The RRR and SSS isomers are commonly referred to as "alpha (α)" dihydrotetrabenazines and can be referred to individually as (+)-α-dihydrotetrabenazine and (−)-α-dihydrotetrabenazine respectively. The alpha isomers are characterised by a trans relative orientation of the hydroxyl and 2-methylpropyl substituents at the 2- and 3-positions—see for example, Kilbourn et al., Chirality, 9:59-62 (1997) and Brossi et al., Helv. Chim. Acta., vol. XLI, No. 193, pp 1793-1806 (1958.

The SRR and RSS isomers are commonly referred to as "beta (β)" isomers and can be referred to individually as (+)-β-dihydrotetrabenazine and (−)-β-dihydrotetrabenazine respectively. The beta isomers are characterised by a cis relative orientation of the hydroxyl and 2-methylpropyl substituents at the 2- and 3-positions.

To date, the literature concerning dihydrotetrabenazines has focussed on the (+)-isomers and in particular on the (+)-α-dihydrotetrabenazine (RRR) isomer and, as far as the present inventors are aware, no therapeutically useful biological activities or therapeutic uses have been disclosed or suggested for the (−)-β-dihydrotetrabenazine isomer.

The Invention

It has now been found that (−)-β-dihydrotetrabenazine isomer is a potent antagonist of the dopamine D4 receptor. Accordingly, it is envisaged that (−)-β-dihydrotetrabenazine isomer is useful in the treatment of conditions in which the D4 receptor or mutant forms thereof are implicated.

The compound (−)-β-dihydrotetrabenazine may be referred to herein variously as "the compound of the invention" or, in the context of pharmaceutical compositions, "the active compound".

Accordingly, in a first Embodiment (Embodiment 1.0), the invention provides (−)-β-dihydrotetrabenazine or a pharmaceutically acceptable salt thereof for use in medicine.

In another Embodiment (Embodiment 1.1), the invention provides a pharmaceutical composition comprising (−)-β-dihydrotetrabenazine or a pharmaceutically acceptable salt thereof and a pharmaceutically acceptable excipient.

In another Embodiment (Embodiment 1.2), the invention provides (−)-β-dihydrotetrabenazine or a pharmaceutically acceptable salt thereof for use as a dopamine D4 receptor antagonist.

In another Embodiment (Embodiment 1.3), the invention provides (−)-β-dihydrotetrabenazine or a pharmaceutically acceptable salt thereof for use in the treatment of a disease or condition selected from psychoses, depression and anxiety.

In further Embodiments (Embodiments 1.4 to 1.19 below) of the Invention, there are provided:

1.4 A method of antagonising a dopamine D4 receptor which method comprises contacting the receptor with (−)-β-dihydrotetrabenazine or a pharmaceutically acceptable salt thereof.

1.5 A method according to Embodiment 1.4 wherein said contacting takes place in vivo in an animal subject.

1.6 A method according to Embodiment 1.5 wherein the animal subject is a mammal.

1.7 A method according to Embodiment 1.6 wherein the mammal is a human.

1.8 (−)-β-Dihydrotetrabenazine or a pharmaceutically acceptable salt thereof for use in the treatment of a disease or condition selected from psychoses, depression and anxiety.

1.9 (−)-β-Dihydrotetrabenazine or a pharmaceutically acceptable salt thereof for use according to Embodiment 1.8 wherein the disease or condition is a psychosis.

1.10 (−)-β-Dihydrotetrabenazine or a pharmaceutically acceptable salt thereof for use according to Embodiment 1.8 wherein the disease or condition is anxiety.

1.11 (−)-β-Dihydrotetrabenazine or a pharmaceutically acceptable salt thereof for use according to Embodiment 1.8 wherein the disease or condition is depression.

1.12 A method of treatment of a disease or condition selected from psychoses, depression and anxiety in a subject in need thereof (e.g. a mammalian subject such as a human), which method comprises administering to the subject a therapeutically effective amount of (−)-β-dihydrotetrabenazine or a pharmaceutically acceptable salt thereof.

1.13 A method according to Embodiment 1.12 wherein the disease or condition is a psychosis.

1.14 A method according to Embodiment 1.12 wherein the disease or condition is anxiety.

1.15 A method according to Embodiment 1.12 wherein the disease or condition is depression.

1.16 The use of (−)-β-dihydrotetrabenazine or a pharmaceutically acceptable salt thereof for the manufacture of a medicament for the treatment of a disease or condition selected from psychoses, depression and anxiety.

1.17 The use according to Embodiment 1.16 wherein the disease or condition is a psychosis.

1.18 The use according to Embodiment 1.16 wherein the disease or condition is anxiety.

1.19 The use according to Embodiment 1.8 wherein the disease or condition is depression.

(−)-β-Dihydrotetrabenazine is believed to have the chemical structure (I) shown in formula (I) below.

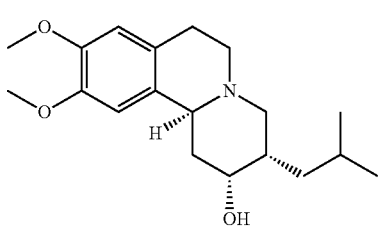

Accordingly, in another Embodiment (Embodiment 1.20), the invention provides an Invention as defined in any one of Embodiments 1.0 to 1.19 wherein the (−)-β-dihydrotetrabenazine has a chemical formula as shown in Formula (1).

In each of the above Embodiments 1.0 to 1.20, the (−)-β-dihydrotetrabenazine or pharmaceutically acceptable salt thereof typically has an isomeric purity of greater than 60%.

The term "isomeric purity" in the present context refers to the amount of (−)-β-DHTBZ dihydrotetrabenazine present relative to the total amount or concentration of dihydrotetrabenazine of all isomeric forms. For example, if 90% of the total dihydrotetrabenazine present in the composition is (−)-β-DHTBZ dihydrotetrabenazine, then the isomeric purity is 90%.

Accordingly, in further Embodiments (Embodiments 1.21 to 1.38) of the Invention, there is provided:

1.21 An Invention as defined in any one of Embodiments 1.0 to 1.20 wherein the (−)-β-DHTBZ has an isomeric purity of greater than 60%.

1.22 An Invention as defined in Embodiment 1.21 wherein the (−)-β-DHTBZ has an isomeric purity of greater than 65%.

1.23 An Invention as defined in Embodiment 1.22 wherein the (−)-β-DHTBZ has an isomeric purity of greater than 70%.

1.24 An Invention as defined in Embodiment 1.21 wherein the (−)-β-DHTBZ has an isomeric purity of greater than 75%.

1.25 An Invention as defined in Embodiment 1.21 wherein the (−)-β-DHTBZ has an isomeric purity of greater than 80%.

1.26 An Invention as defined in Embodiment 1.21 wherein the (−)-β-DHTBZ has an isomeric purity of greater than 85%.

1.27 An Invention as defined in Embodiment 1.21 wherein the (−)-β-DHTBZ has an isomeric purity of greater than 90%.

1.28 An Invention as defined in Embodiment 1.21 wherein the (−)-β-DHTBZ has an isomeric purity of greater than 91%.

1.29 An Invention as defined in Embodiment 1.21 wherein the (−)-β-DHTBZ has an isomeric purity of greater than 92%.

1.30 An Invention as defined in Embodiment 1.21 wherein the (−)-β-DHTBZ has an isomeric purity of greater than 93%.

1.31 An Invention as defined in Embodiment 1.21 wherein the (−)-β-DHTBZ has an isomeric purity of greater than 94%.

1.32 An Invention as defined in Embodiment 1.21 wherein the (−)-β-DHTBZ has an isomeric purity of greater than 95%.

1.33 An Invention as defined in Embodiment 1.21 wherein the (−)-β-DHTBZ has an isomeric purity of greater than 96%.

1.34 An Invention as defined in Embodiment 1.21 wherein the (−)-β-DHTBZ has an isomeric purity of greater than 97%.

1.35 An Invention as defined in Embodiment 1.21 wherein the (−)-β-DHTBZ has an isomeric purity of greater than 98%.

1.36 An Invention as defined in Embodiment 1.21 wherein the (−)-β-DHTBZ has an isomeric purity of greater than 99%.

1.37 An Invention as defined in Embodiment 1.21 wherein the (−)-β-DHTBZ has an isomeric purity of greater than 99.5%.

1.38 An Invention as defined in Embodiment 1.21 wherein the (−)-β-DHTBZ has an isomeric purity of greater than 99.9%.

Pharmaceutically Acceptable Salts

Unless the context requires otherwise, a reference in this application to (−)-β-dihydrotetrabenazine, includes within its scope not only the free base of the (−)-β-dihydrotetrabenazine but also its salts, and in particular acid addition salts.

Accordingly, in further Embodiments (Embodiments 1.39 to 1.41) of the Invention, there is provided:

1.39 An invention as defined in any one of Embodiments 1.0 to 1.38 wherein the (−)-β-dihydrotetrabenazine is in the form of a free base.

1.40 An invention as defined in any one of Embodiments 1.0 to 1.38 wherein the (−)-β-dihydrotetrabenazine is in the form of a pharmaceutically acceptable salt.

1.41 An invention as defined in Embodiment 1.40 wherein the pharmaceutically acceptable salt is an acid addition salt.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethane-suiphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are pharmaceutically acceptable salts, and examples of pharmaceutically acceptable salts are discussed in Berge et al., 1977, "Pharmaceutically Acceptable Salts," *J. Pharm. Sci., Vol.* 66, pp. 1-19.

Particular acids from which the acid addition salts are formed include acids having a pKa value of less than 3.5 and more usually less than 3. For example, the acid addition salts can be formed from an acid having a pKa in the range from +3.5 to −3.5.

Acid addition salts can be prepared by the methods described herein or conventional chemical methods such as the methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the appropriate base or acid in water or in an organic solvent, or in a mixture of the two; generally, nonaqueous media such as ether, ethyl acetate, ethanol, isopropanol, or acetonitrile are used.

Isotopes

The (−)-β-dihydrotetrabenazine may contain one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{11}C$, 12C, $^{13}C$ and $^{14}C$ and $^{16}O$ and $^{18}O$.

In an analogous manner, a reference to a particular functional group also includes within its scope isotopic variations, unless the context indicates otherwise.

For example, a reference to an alkyl group such as an ethyl group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group).

The isotopes may be radioactive or non-radioactive. In one embodiment of the invention, the compound of any one of Embodiments 1.0 to 1.38 contains no radioactive isotopes. Such compounds are preferred for therapeutic use. In another embodiment, however, the compound of any one of Embodiments 1.0 to 1.38 may contain one or more radioisotopes. Compounds containing such radioisotopes may be useful in a diagnostic context.

Solvates (−)-β-Dihydrotetrabenazine in any one of Embodiments 1.0 to 1.38 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Alternatively, rather than existing as a hydrate, the compound of the invention may be anhydrous. Therefore, in another embodiment, the compound of formula (1) as defined in any one of Embodiments 1.0 to 1.38 is in an anhydrous form.

Methods for Preparation of (−)-β-dihydrotetrabenazine (−)-β-Dihydrotetrabenazine (compound of formula (I)) can be prepared from tetrabenazine according to the synthetic route shown in Scheme 1.

Scheme 1

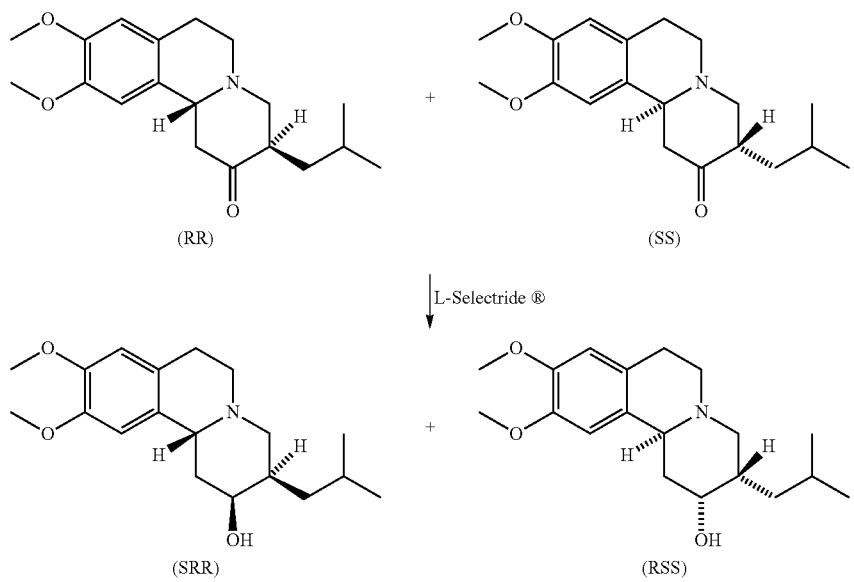

(RR)

(SS)

L-Selectride ®

(SRR)

(RSS)

-continued

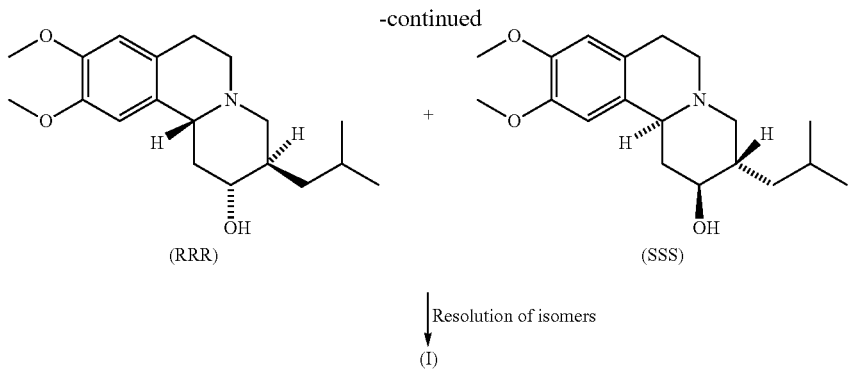

(RRR) + (SSS)

↓ Resolution of isomers (I)

Racemic tetrabenazine (3-isobutyl-9,10-dimethyoxy-1,3,4,6,7,11b-hexahydro-2H-pyrido[2,1,a]isoquinolin-2-one) containing the RR and SS isomers of tetrabenazine is reduced with L-Selectride® to afford a mixture of four dihydrotetrabenazine isomers of which a racemic mixture of the β-dihydrotetrabenazines (SRR and RSS isomers) constitutes the major product and a racemic mixture of the α-dihydrotetrabenazines (the RRR and SSS isomers) constitutes a minor product. The α-dihydrotetrabenazines can be removed during an initial purification procedure, for example by chromatography or recrystallization and then the racemic β-dihydrotetrabenazines resolved (e.g. by recrystallisation with di-p-toluoyl-R-tartaric acid or (S)-(+)-camphorsulfonic acid or by chiral chromatography), to afford (−)-β-dihydrotetrabenazine (I) ((2S,3R,11bR)-3-isobutyl-9,10-dimethoxy-1,3,4,6,7,11b-hexahydro-2H-pyrido[2,1,a]isoquinolin-2-ol). The stereochemical configuration of (−)-β-dihydrotetrabenazine can be determined, so example by forming a salt such as the mesylate salt in crystalline form and the structure identified by X-ray crystallography.

(−)-β-Dihydrotetrabenazine can also be prepared according to Yao et al., "Preparation and evaluation of tetrabenazine enantiomers and all eight stereoisomers of dihydrotetrabenazine as VMAT2 inhibitors", Eur. J. Med. Chem., (2011), 46, pp. 1841-1848.

Biological Properties and Therapeutic Uses (−)-β-Dihydrotetrabenazine and its pharmaceutically acceptable salts are antagonists of the dopamine D4 receptor.

As described in Example 1 below, (−)-β-Dihydrotetrabenazine has been found to exhibit 99% inhibition of the D4 receptor at a concentration of 10 µM and 87% inhibition at a concentration of 1 µM. By comparison, the (+)-α-dihydrotetrabenazine and (+)-β-dihydrotetrabenazine are essentially inactive at the dopamine D4 receptor and the (−)-α-dihydrotetrabenazine isomer is significantly less active than the (−)-β-dihydrotetrabenazine isomer. Thus, as described in Example 1, the (−)-α-dihydrotetrabenazine isomer exhibited 19% inhibition of the D4 receptor at a concentration of 1 µM, compared to a figure of 87% inhibition at the same concentration exhibited by the (−)-β-dihydrotetrabenazine isomer.

In addition, as demonstrated in Example 1 below, (−)-β-Dihydrotetrabenazine and its pharmaceutically acceptable salts are also potent antagonists of the alpha 2A receptor, the alpha 2C receptor, and are potent agonists of the 5-HT 1A and 5-HT 2B receptors.

On the basis of its receptor binding profiles and, in particular its activity at the dopamine D4 receptor, it is envisaged that (−)-β-dihydrotetrabenazine and its pharmaceutically acceptable salts will be useful in the treatment of psychoses, anxiety and depression.

Accordingly, in further Embodiments (Embodiments 1.42 to 1.53) of the Invention, there is provided:

1.42 (−)-β-Dihydrotetrabenazine or a pharmaceutically acceptable salt thereof for use in the prophylaxis or treatment of psychosis.

1.43 (−)-β-Dihydrotetrabenazine or a pharmaceutically acceptable salt thereof for use in preventing or alleviating psychosis.

1.44 (−)-β-Dihydrotetrabenazine or a pharmaceutically acceptable salt thereof for use in preventing, alleviating or reducing one or more symptoms of schizophrenia.

1.45 The use of (−)-β-dihydrotetrabenazine or a pharmaceutically acceptable salt thereof for the manufacture of a medicament for the prophylaxis or treatment of psychosis.

1.46 A method for the prophylaxis or treatment of psychosis, the method comprising administering to the mammal a therapeutically effective amount of (−)-β-dihydrotetrabenazine or a pharmaceutically acceptable salt thereof.

1.47 The use of (−)-β-dihydrotetrabenazine or a pharmaceutically acceptable salt thereof for the manufacture of a medicament for preventing or alleviating a psychotic episode.

1.48 A method for preventing or alleviating a psychotic episode, the method comprising administering to the mammal a therapeutically effective amount of (−)-β-dihydrotetrabenazine or a pharmaceutically acceptable salt thereof.

1.49 A method or use as defined in any one of Embodiments 1.42 to 1.48 wherein the psychosis or psychotic episode arises from or is associated with schizophrenia.

1.50 The use of (−)-β-dihydrotetrabenazine or a pharmaceutically acceptable salt thereof for the manufacture of a medicament for the prophylaxis or treatment of schizophrenia.

1.51. A method for the prophylaxis or treatment of schizophrenia, the method comprising administering to the mammal a therapeutically effective amount of (−)-β-dihydrotetrabenazine or a pharmaceutically acceptable salt thereof.

1.52 The use of (−)-β-dihydrotetrabenazine or a pharmaceutically acceptable salt thereof for the manufacture of a medicament for preventing, alleviating or reducing one or more symptoms of schizophrenia.

1.53 A method for preventing, alleviating or reducing one or more symptoms of schizophrenia, the method comprising administering to the mammal a therapeutically effective amount of (−)-β-dihydrotetrabenazine or a pharmaceutically acceptable salt thereof.

In each of Embodiments 1.3, 1.8, 1.9, 1.12, 1.13, 1.16, 1.17 and 1.42 to 1.53, the psychotic episodes, psychoses or symptoms prevented, alleviated or reduced in accordance with the invention may be any one or more symptoms selected from:
- delusions;
- hallucinations;
- visual hallucinations;
- auditory hallucinations;
- hallucinations involving tactile sensations, tastes or smells;
- confusion;
- emotional, behavioural, or intellectual disturbances;
- withdrawal from reality;
- illogical and/or disorganized patterns of thinking;
- paranoid or delusional beliefs;
- paranoia
- grandiose delusions;
- persecutory or self-blaming delusions; and
- personality changes.

In each of Embodiments 1.3, 1.8, 1.9, 1.12, 1.13, 1.16, 1.17 and 1.42 to 1.53, the psychotic episodes, psychoses or symptoms prevented, alleviated or reduced in accordance with the invention may be any one or more selected from those arising from or associated with:
- psychosis caused by or associated with schizophrenia;
- psychosis caused by or associated with bipolar disorder (manic depression);
- psychosis caused by or associated with severe clinical depression;
- psychosis induced by disorders and conditions such as:
  - electrolyte disorder;
  - urinary tract infections in the elderly;
  - pain syndromes;
  - drug toxicity;
  - drug withdrawal; and
  - infections of or injuries to the brain;
- psychosis caused by chronic psychological stress (brief reactive psychosis);
- psychosis triggered or exacerbated by severe mental stress; and
- psychosis triggered by or arising from or following illnesses and conditions such as AIDS, leprosy, malaria and mumps.

In each of Embodiments 1.3, 1.8, 1.9, 1.12, 1.13, 1.16, 1.17 and 1.42 to 1.53, the symptoms or psychoses may arise from or be associated with schizophrenia and may be any one or more symptoms selected from:
- delusions;
- hallucinations;
- confusion;
- emotional, behavioral, or intellectual disturbances;
- withdrawal from reality; and
- illogical patterns of thinking.

The (−)-β-Dihydrotetrabenazine and its salts may also be used for the treatment of anxiety. Accordingly, in further Embodiments (Embodiments 1.54 to 1.59) of the Invention, there is provided:

1.54 (−)-β-Dihydrotetrabenazine or a pharmaceutically acceptable salt thereof for use in alleviating or preventing any one or more symptoms of anxiety.

1.55 (−)-β-Dihydrotetrabenazine or a pharmaceutically acceptable salt thereof for use as defined in Embodiment 1.54 wherein the anxiety is secondary to other psychiatric illness.

1.56 (−)-β-Dihydrotetrabenazine or a pharmaceutically acceptable salt thereof for use as defined in Embodiment 1.54 wherein the anxiety is primary anxiety.

1.57 (−)-β-Dihydrotetrabenazine or a pharmaceutically acceptable salt thereof for use as defined in Embodiment 1.54 wherein the anxiety is associated with a neurosis.

1.58 (−)-β-Dihydrotetrabenazine or a pharmaceutically acceptable salt thereof for use as defined in Embodiment 1.54 wherein the anxiety is phobic anxiety, for example wherein the phobic anxiety arises from social phobias, general phobias and specific phobias.

1.59 (−)-β-Dihydrotetrabenazine or a pharmaceutically acceptable salt thereof for use as defined in Embodiment 1.54 wherein the anxiety arises from an obsessional disorder.

The (−)-β-Dihydrotetrabenazine (or a pharmaceutically acceptable salt thereof) may be used to prevent, stop or alleviate any one or more mental symptoms arising from or associated with anxiety such as anger, fear, apprehension, or worry, loss of patience, concentration difficulties, anxiety-related sleeping difficulties, anxiety-related depression, and/or obsessive behaviour development.

The (−)-β-Dihydrotetrabenazine (or a pharmaceutically acceptable salt thereof) may be used to prevent, stop or alleviate any one or more physical symptoms arising form or associated with anxiety such as heart palpitations, pale skin, sweating, nausea, chest pain, shortness of breath, stomach aches, headache, excessive thirst, flatulence, diarrhea, increased frequency of urination, sexual impotence, muscle pain, dizziness, pins and needles, tremors and painful or absent periods In each of Embodiments 1.42 to 1.59, the (−)-β-dihydrotetrabenazine or a pharmaceutically acceptable salt thereof may have a purity as defined in any one of Embodiments 1.21 to 1.38 and/or a chemical structure as defined in Embodiment 1.20.

The suitability as an anxiolytic can be tested using the by the elevated plus maze paradigm which has been widely used as a test for anxiety, as it avoids confounding effects on consummatory responses or sensitivity to shock and it has a certain level of ethological relevance (see Rodgers R J, Cole J C (1994) The elevated plus maze. Pharmacological methods and ethology. In: Cooper, S J, Hendrie C A (eds) Ethology and Psychopharmacology. J. Wiley & Sons Ltd, pp 9-941994).

The maze consists of opposite pairs of open and closed arms, and the proportion of exploration carried out on the open arms is taken to be a measure of anxiety. Thus the percentage of open arm entries is increased by known anxiolytic agents and reduced by anxiogenic compounds (Pellow, S, Chopin P, File S E, Briley, M (1985) Validation of open: closed arm entries in an elevated plus maze as a measure of anxiety in the rat. J. Neurosci. Meth. 14: 149-167). In addition, the plus maze may be used to examine the behavioural response to stress, as exposure induces the release of corticosterone File, SE, Pellow, S (1987) Behavioural pharmacology of minor tranquilisers. J. Pharmacol. Exp. Ther. 35: 265-290). The elevated plus maze is based on an approach conflict model and has been validated as a model of anxiety in the rat (Tomkins D M (1990) The behavioural effects of anxiogenic agents in rodents. PhD thesis. Postgraduate studies in Pharmacology. University of Bradford).

Pharmaceutical Formulations and Methods of Treatment

The pharmaceutical compositions of the Invention can be in any form suitable for oral, parenteral, topical, intranasal, intrabronchial, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery.

Pharmaceutical dosage forms suitable for oral administration include tablets, capsules, caplets, pills, lozenges, syrups, solutions, sprays, powders, granules, elixirs and suspensions, sublingual tablets, sprays, wafers or patches and buccal patches.

Pharmaceutical compositions containing the dihydrotetrabenazine compound of the invention can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, e.g.; lactose, sucrose, sorbitol or mannitol; and/or a non-sugar derived diluent such as sodium carbonate, calcium phosphate, talc, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (e.g.; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped mouldable or waxy material containing the active compound.

Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose.

Particular pharmaceutical compositions of the invention are compositions selected from:
  Sublingual compositions;
  Intranasal;
  Pellets or tablets formulated to provide release kinetics corresponding to zero order release of the active compound;
  Pellets or tablets formulated to provide first fast release followed by constant rate release (zero order) of the active compound;
  Pellets or tablets formulated to provide a mixture of first order and zero order release of the active compound; and
  Pellets or tablets formulated to provide a combination of zero order and first order release of the active compound; and optionally a further order of release of the active compound selected from second, third and fourth orders of release and combinations thereof.

Pellets and tablets formulated to provide release kinetics of the types defined above can be prepared according to methods well known the skilled person; for example as described in Remington's Pharmaceutical Sciences (idem) and "Remington—The Science and Practice of Pharmacy, $21^{st}$ edition, 2006, ISBN 0-7817-4673-6.

The compound of the invention will generally be presented in unit dosage form and, as such, will typically contain sufficient compound to provide a desired level of biological activity. For example, a formulation intended for oral administration may contain from 2 milligrams to 200 milligrams of active ingredient, more usually from 10 milligrams to 100 milligrams, for example, 12.5 milligrams, 25 milligrams and 50 milligrams.

The active compound will be administered to a patient in need thereof (for example a human or animal patient) in an amount sufficient to achieve the desired therapeutic effect.

The compound will generally be administered to a subject in need of such administration, for example a human or animal patient, preferably a human.

The compound of the invention will typically be administered in amounts that are therapeutically or prophylactically useful and which generally are non-toxic. However, in certain situations, the benefits of administering a dihydrotetrabenazine compound of the invention may outweigh the disadvantages of any toxic effects or side effects, in which case it may be considered desirable to administer compounds in amounts that are associated with a degree of toxicity.

A typical daily dose of the compound of the invention can be in the range from 0.025 milligrams to 5 milligrams per kilogram of body weight, for example up to 3 milligrams per kilogram of bodyweight, and more typically 0.15 milligrams to 5 milligrams per kilogram of bodyweight although higher or lower doses may be administered where required.

By way of example, an initial starting dose of 12.5 mg may be administered 2 to 3 times a day. The dosage can be increased by 12.5 mg a day every 3 to 5 days until the maximal tolerated and effective dose is reached for the individual as determined by the physician. Ultimately, the quantity of compound administered will be commensurate with the nature of the disease or physiological condition being treated and the therapeutic benefits and the presence or absence of side effects produced by a given dosage regimen, and will be at the discretion of the physician.

EXAMPLES

Example 1

Receptor Protein Binding Studies

The four 3,11b trans-dihydrotetrabenazine isomers (+)-α, (−)-α, (+)-β and (−)-β were subjected to specific binding assays to test their ability to bind to the receptors and transporter proteins described below. The results are set out in Table 1

TABLE 1

Percentage Inhibition by Solutions of Dihydrotetrabenazine isomers of Specific Binding at Receptor Proteins

| RECEPTOR | CONC | (−)-Beta | (−)-Alpha | (+)-Beta | (+)-Alpha |
|---|---|---|---|---|---|
| | | | % Inhibition | | |
| alpha 1A (h) (antagonist radioligand) | 1.0E−06 | 21 | 1 | 2 | 7 |
| | 1.0E−05 | 75 | 6 | 33 | 12 |
| alpha 1B (h) (antagonist radioligand) | 1.0E−06 | 10 | 9 | 3 | −4 |
| | 1.0E−05 | 60 | 14 | 1 | 23 |
| alpha 1D (h) (antagonist radioligand) | 1.0E−06 | 24 | 13 | 18 | 15 |
| | 1.0E−05 | 73 | 25 | 20 | −10 |
| alpha 2A (h) (antagonist radioligand) | 1.0E−06 | 63 | 30 | −1 | 5 |
| | 1.0E−05 | 95 | 65 | 11 | 7 |
| alpha 2B (h) (antagonist radioligand) | 1.0E−06 | 6 | −22 | −19 | −17 |
| | 1.0E−05 | 57 | 8 | −1 | −11 |
| alpha 2C (h) (antagonist radioligand) | 1.0E−06 | 70 | 17 | −7 | 4 |
| | 1.0E−05 | 95 | 69 | 12 | 5 |
| D1 (h) (antagonist radioligand) | 1.0E−06 | 36 | 5 | 0 | 0 |
| | 1.0E−05 | 88 | 45 | 8 | −2 |
| D2S (h) (antagonist radioligand) | 1.0E−06 | 56 | 22 | −8 | −1 |
| | 1.0E−05 | 92 | 73 | 7 | 7 |
| D3 (h) (antagonist radioligand) | 1.0E−06 | 19 | 26 | −18 | −14 |
| | 1.0E−05 | 76 | 79 | 12 | 2 |
| D4.4 (h) (antagonist radioligand) | 1.0E−06 | 87 | 19 | −3 | −3 |
| | 1.0E−05 | 99 | 65 | 2 | −7 |
| D5 (h) (antagonist radioligand) | 1.0E−06 | 35 | −3 | −8 | −7 |
| | 1.0E−05 | 95 | 23 | −5 | −8 |
| Dopamine D2L | 1.0E−06 | 55 | 27 | 1 | 10 |
| | 1.0E−05 | 89 | 68 | 18 | 14 |
| I2 (antagonist radioligand) | 1.0E−06 | 11 | 13 | 6 | 1 |
| | 1.0E−05 | 37 | 12 | 11 | 20 |
| mu (MOP) (h) (agonist radioligand) | 1.0E−06 | 4 | 11 | 7 | 0 |
| | 1.0E−05 | 39 | 2 | 2 | 5 |
| 5-HT1A(h) (agonist radioligand) | 1.0E−06 | 68 | 80 | 20 | 38 |
| | 1.0E−05 | 97 | 96 | 64 | 83 |
| 5-HT2B (h) (agonist radioligand) | 1.0E−06 | 79 | 55 | −2 | −4 |
| | 1.0E−05 | 98 | 92 | −7 | 0 |
| 5-HT2C (h) (agonist radioligand) | 1.0E−06 | 21 | 0 | 2 | −8 |
| | 1.0E−05 | 72 | 16 | −5 | 3 |
| 5-HT4e (h) (antagonist radioligand) | 1.0E−06 | −4 | 4 | −4 | 2 |
| | 1.0E−05 | 19 | 26 | 19 | 40 |
| 5-HT5A(h) | 1.0E−06 | −8 | −24 | −23 | −26 |
| | 1.0E−05 | 45 | −6 | −13 | −2 |
| 5-HT6 (h) | 1.0E−06 | 22 | 6 | 15 | −1 |
| | 1.0E−05 | 78 | 29 | 6 | 35 |
| Sigma 1 (h) (agonist radioligand) | 1.0E−06 | 82 | 40 | 92 | 64 |
| | 1.0E−05 | 99 | 78 | 99 | 96 |
| Sigma 2 (h) (agonist radioligand) | 1.0E−06 | 73 | 52 | 41 | 34 |
| | 1.0E−05 | 99 | 85 | 85 | 70 |
| hERG (membrane preparation) (antagonist radioligand) | 1.0E−06 | −1 | 5 | 3 | 2 |
| | 1.0E−05 | 64 | 19 | 8 | 33 |

The results demonstrate that (−)-β-dihydrotetrabenazine is more active than (+)-β-dihydrotetrabenazine, (−)-α-dihydrotetrabenazine and (+)-α-dihydrotetrabenazine as an antagonist at the alpha-1A, alpha-1B, alpha 1D, alpha 2C, dopamine D1, D2S, D2L, D4 and D5 receptors.

On the basis of the receptor binding profile of (−)-β-dihydrotetrabenazine, it is considered that the compound will be useful in the treatment of psychoses and other diseases and conditions in which the dopamine D4 receptor plays a part.

EQUIVALENTS

It will readily be apparent that numerous modifications and alterations may be made to the specific embodiments of the invention described above without departing from the principles underlying the invention. All such modifications and alterations are intended to be embraced by this application.

The invention claimed is:

1. A method of antagonizing a dopamine D4 receptor which method comprises contacting the receptor with (−)-β-dihydrotetrabenazine or a pharmaceutically acceptable salt thereof.

2. A method of treating a disease or condition selected from psychoses, depression and anxiety in a subject in need thereof, the method comprising administering an effective amount of (−)-β-dihydrotetrabenazine or a pharmaceutically acceptable salt thereof to the subject.

3. A method according to claim 2 wherein the disease or condition is a psychosis.

4. A method according to claim 1 wherein contacting of dopamine D4 receptors with (−)-β-dihydrotetrabenazine or a pharmaceutically acceptable salt thereof takes place in vivo in a mammalian subject.

5. A method according to claim 4 wherein the mammalian subject is a human.

6. A method according to claim 5 wherein the in vivo contacting of dopamine D4 receptors with (−)-β-dihydrotetrabenazine or a pharmaceutically acceptable salt thereof is effective to treat a condition from which the human subject is suffering in which the D4 receptor or mutant forms thereof are implicated, said condition being selected from psychoses, depression and anxiety.

7. A method according to claim 1 wherein the (−)-β-dihydrotetrabenazine has an isomeric purity of greater than 90%.

8. A method according to claim 7 wherein the (−)-β-dihydrotetrabenazine has an isomeric purity of greater than 95%.

9. A method according to claim 6 wherein the (−)-β-dihydrotetrabenazine has an isomeric purity of greater than 90%.

10. A method according to claim 9 wherein the (−)-β-dihydrotetrabenazine has an isomeric purity of greater than 95%.

* * * * *